United States Patent [19]

Gough

[11] 4,383,991

[45] May 17, 1983

[54] O-ALKYL-S-ALKYL-S-BRANCHED ALKYLPHOSPHORODITHIOATE SOIL INSECTICIDES

[75] Inventor: Stanley T. D. Gough, Whitehouse Station, N.J.

[73] Assignee: Rhone-Poulenc Agrochimie, Lyons, France

[21] Appl. No.: 276,622

[22] Filed: Jun. 23, 1981

[51] Int. Cl.³ .................. A01N 57/12; C07F 9/165
[52] U.S. Cl. ..................... 424/224; 260/963
[58] Field of Search ............................. 260/963

[56] References Cited

U.S. PATENT DOCUMENTS 4,273,769  1/1981  Koyanagi et al. .................. 260/963

Primary Examiner—Anton H. Sutto
Attorney, Agent, or Firm—Burns, Doane, Swecker & Mathis

[57] ABSTRACT

This invention provides compounds having the formula:

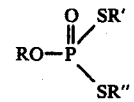

wherein R and R' are the same or different $C_1$–$C_3$ n-alkyl and R" is $C_3$–$C_4$ branched alkyl. It also provides for a method of corn rootworm control with such compounds.

11 Claims, No Drawings

O-ALKYL-S-ALKYL-S-BRANCHED ALKYLPHOSPHORODITHIOATE SOIL INSECTICIDES

BACKGROUND OF THE INVENTION

1. Field of the Invention

This invention is concerned with phosphorodithioates having an S-branched alkyl group.

2. Description of the Prior Art

The compound that is closely related to the compounds of this invention is ethoprop, wich does not have an S-branched alkyl group. The compounds of this invention are more active against corn rootworm.

SUMMARY OF THE INVENTION

This invention provides compounds having the formula:

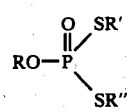

wherein R and R' are the same or different $C_1$–$C_3$ n-alkyl and R" is $C_3$–$C_4$ branched alkyl. It also provides for a method of corn rootworm control with such compounds.

DESCRIPTION OF SPECIFIC EMBODIMENTS

The compounds of this invention can be prepared by synthesis methods well known in the art. For example, an O-alkyl-S-alkyl-phosphorochloridate can be reacted with the alkali metal (e.g., sodium) salt of isopropyl mercaptan or isobutyl mercaptan, generally at ambient temperatures.

The organophosphorus compounds of the invention have been found useful for the control of corn rootworm at concentrations of from 0.05 to 1 ppm of the total formulation. Because of the low rates required for effective control, it would be impracticable to apply the compounds as such. It is desirable, therefore, to apply them in the form of liquid sprays, or as formulations containing solid vehicles or extenders, in either case the formulation comprising a minor amount of the active ingredient. For example, the compounds may be mixed with a finely divided solid carrier as an aid in uniform distribution. As a general rule, acceptable solid carriers are those which are non-hygroscopic (to prevent caking) and inert (to eliminate undesirable adverse effects upon the formulation itself and upon the environment to be treated). Some of the useful solid carriers are finely ground koalinite, bentonite, talc, attapulgite, and the like. When making up a solid formulation, a more even distribution of chemical can be obtained if it is dissolved in a volatile solvent prior to mixing. After mixing, the solvent is evaporated by any convenient method. Any solvent in which the active ingredient is soluble and which may be readily removed is acceptable provided it does not leave any residue which in itself is toxic.

Liquid compositions of the active components of the invention may be dispersions or emulsions. Since the useful compounds disclosed herein are substantially insoluble in water, it is desirable to add a small amount of an inert, non-phytotoxic organic solvent which can be readily dispersed in the aqueous medium to produce a uniform dispersion. An effective liquid formulation includes the active component, acetone, water, and a surface active agent such as Tween-20 (polyoxyethylene sorbitan monolaurate). Included among the other surface active agents which the art will recognize as useful are Atlox G-3396 and Atlox G-2081, which are, respectively, a blend of polyoxyethylene sorbitol esters and esters of mixed fatty and resin acids and alkyl aryl sulfonates, and a blend of polyoxyethylene sorbitan esters of fatty and resin acids and alkyl aryl sulfonates.

EXAMPLE 1

The sodium salt of t-butyl mercaptan (3.6 g.) was added to O-ethyl-S-propylphosphorochloridate (6.5 g.) in toluene (100 ml.). The mixture exothermed to 32° C. and was stirred overnight at room temperature. The mixture was then filtered and evaporated, and the residue dissolved in chloroform (100 ml.) washed with water, the chloroform dried and evaporated, and the product O-ethyl-S-propyl-S-t-butyl phosphorodithioate distilled, bp 120°/0.4 mm. The yield was 1.1 g. and the product had been expected NMR—O$CH_2$ multiplet at 4.3 ppm, S—$CH_2$ multiplet at 2.9 ppm, S—C—C—$CH_3$ triplet at 1.0 ppm, O—C—$CH_3$ split triplet at 1.4 ppm, S+ doublet at 1.6 ppm, S—C—$CH_2$ multiplet at 1.8 ppm, other protons multiplet at 1.4 ppm.

EXAMPLE 2 i-Propyl mercaptan (11.5 g.) was added to sodium hydride (3.6 g.) in toluene, and the mixture was heated at 40° C. under nitrogen until gas evolution ceased. O-ethyl-S-propyl-phosphorochloridate (3.0 g.) was added to the mixture at 25° C. and an exotherm to 31° C. occurred. The reaction was then worked up as above to give the product, O-ethyl-S-propyl-S-i-propyl-phosphorodithioate.

Corn Rootworm Intrinsic Activity

The test compound is prepared in a one percent solution with acetone or ethanol. The stock solution is then diluted with an aqueous solution of Tween-20 and water to the appropriate concentration (i.e., 1, 0.1, or 0.05 ppm.). Two ml. of this solution is pipetted into a 9 cm. petri dish containing two layers of filter paper. Second instar larvae are introduced and the dish closed. Observations for mortality and moribund larvae are made after two days' (48 hours) exposure. Activity is primarily contact and vapor action with minimum ingestion. The results are tabulated in the Table, as percent kill.

TABLE

| Corn Rootworm Data (Intrinsic) | ppm | | |
|---|---|---|---|
| | 1 | .1 | .05 |
| Compound of Example 1 | 100 | 70 | — |
| Compound of Example 2 | 100 | 30 | — |
| Ethoprop | 100 | 10 | 0 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for controlling corn rootworm which comprises applying to its habitat, in an amount effective for controlling corn rootworm, a compound having the formula

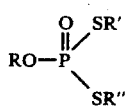

wherein R is ethyl, R' is n-propyl and R" is $C_3$–$C_4$ branched alkyl.

2. The method according to claim 1, wherein R" is i-propyl.

3. A method for controlling corn rootworm which comprises applying to its habitat, in an amount effective for controlling corn rootworm, a compound having the formula

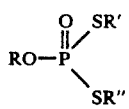

wherein R and R', which can be the same or different, are $C_1$–$C_3$ n-alkyl and R" is branched butyl.

4. A method according to claim 3, wherein R is ethyl and R' is n-propyl.

5. The method according to claim 3, wherein R is ethyl, R' is n-propyl and R" is t-butyl.

6. A compound having the formula

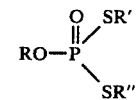

wherein R and R', which can be the same or different, are $C_1$–$C_3$ n-alkyl and R" is branched butyl.

7. A compound according to claim 6, wherein R is ethyl and R' is n-propyl.

8. The compound according to claim 6, wherein R is ethyl, R' is n-propyl and R" is t-butyl.

9. A composition for use in controlling corn rootworm comprising, as the active ingredient, a compound having the formula

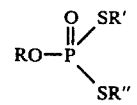

wherein R and R', which can be the same or different, are $C_1$–$C_3$ n-alkyl and R" is branched butyl, in an amount effective for controlling corn rootworm, together with an inert, non-phytotoxic carrier therefor.

10. A composition according to claim 9, wherein R is ethyl and R' is n-propyl.

11. The composition according to claim 9, wherein R is ethyl, R' is n-propyl and R" is t-butyl.

* * * * *